US008578960B2

(12) United States Patent
Davis, Jr.

(10) Patent No.: US 8,578,960 B2
(45) Date of Patent: Nov. 12, 2013

(54) GAS SUPPLY SYSTEM

(76) Inventor: Thomas Oliver Davis, Jr., Orient, OH (US)

( * ) Notice: Subject to any disclaimer, the term of this patent is extended or adjusted under 35 U.S.C. 154(b) by 0 days.

(21) Appl. No.: 13/409,617

(22) Filed: Mar. 1, 2012

(65) Prior Publication Data

US 2012/0168002 A1 Jul. 5, 2012

Related U.S. Application Data

(63) Continuation of application No. 12/115,842, filed on May 6, 2008, now abandoned.

(51) Int. Cl.
*B65H 75/40* (2006.01)
*B65H 75/14* (2006.01)
*B65H 75/30* (2006.01)
*B65H 75/42* (2006.01)

(52) U.S. Cl.
USPC ............ 137/355.26; 137/355.21; 137/355.23; 242/404.2

(58) Field of Classification Search
USPC ............... 137/355.16–355.2, 355.23, 355.24, 137/355.26–355.28, 355.21; 242/404.2
See application file for complete search history.

(56) References Cited

U.S. PATENT DOCUMENTS

| 794,399 | A | * | 7/1905 | Erxleben ................. 137/355.26 |
| 1,045,069 | A | * | 11/1912 | Nuhring ................... 137/355.26 |
| 1,077,146 | A | * | 10/1913 | Lemon .......................... 15/3.53 |
| 1,502,518 | A | * | 7/1924 | Nasta .......................... 242/129.6 |
| 1,675,140 | A | * | 6/1928 | Schenderlein ............. 242/376.1 |
| 1,683,911 | A | * | 9/1928 | Morris .......................... 239/196 |
| 1,746,995 | A | * | 2/1930 | Edwards ................... 137/355.17 |
| 2,596,766 | A | * | 5/1952 | Dugdale .................... 242/407.1 |
| 2,711,734 | A | | 6/1955 | Moe |
| 2,904,272 | A | | 9/1959 | Barrett |
| 3,184,180 | A | * | 5/1965 | Rockwell ................... 242/399.2 |
| 3,437,105 | A | * | 4/1969 | Stracek .................... 137/355.23 |

(Continued)

FOREIGN PATENT DOCUMENTS

EP 2116270 A1 11/2009

OTHER PUBLICATIONS

European Search Report for European Patent Appl. No. EP 09 25 1055.1, dated Jul. 10, 2009.

(Continued)

*Primary Examiner* — Eric Keasel
*Assistant Examiner* — Jonathan Waddy
(74) *Attorney, Agent, or Firm* — The Law Office of Patrick F. O'Reilly III, LLC

(57) ABSTRACT

A gas supply system in the form of a winding device that includes a housing with an aperture, a spool, a one way bearing, an interval locking device, a universal shaft, a spring housing, a spring torque spool and a pair of spring grounding tabs, a main base that stabilizes the housing, a rotating shaft where the main base is disposed on the distal end of the rotating shaft, a rotational bearing that is disposed on the proximal end of the rotating shaft and connects the rotating shaft to the base clamp. The base clamp has a pair of corresponding apertures and secures the gas supply system to a tubular shaped object, and includes an adjustable clamp screw that has a handle and a threaded bolt wherein the proximal end of the threaded bolt is attached to and perpendicularly extends from the handle and the adjustable clamp screw.

20 Claims, 4 Drawing Sheets

(56) References Cited

U.S. PATENT DOCUMENTS

| | | | |
|---|---|---|---|
| 4,757,838 A * | 7/1988 | McGullion | 137/355.27 |
| 5,390,695 A | 2/1995 | Howard | |
| 5,392,808 A | 2/1995 | Pierce | |
| 5,787,923 A * | 8/1998 | Shea et al. | 137/355.26 |
| 5,826,608 A | 10/1998 | Pierce | |
| 5,975,120 A | 11/1999 | Novosel | |
| 6,065,490 A | 5/2000 | Falcone, Jr. | |
| 6,095,922 A | 8/2000 | Friedrichsen et al. | |
| 6,478,265 B2 * | 11/2002 | Leach | 248/75 |
| 6,588,444 B2 | 7/2003 | Paplow et al. | |
| 6,591,858 B2 | 7/2003 | Peterson | |
| 6,889,688 B1 | 5/2005 | Wright | |
| 6,978,960 B2 * | 12/2005 | Schaller | 242/385.3 |
| 7,104,491 B2 * | 9/2006 | Vinding | 242/378.4 |
| 7,216,665 B1 | 5/2007 | Sims, Jr. | |
| 7,857,000 B1 | 12/2010 | Langdon | |
| 2002/0195143 A1 | 12/2002 | Paplow et al. | |
| 2003/0146332 A1 | 8/2003 | Vinding | |
| 2005/0178440 A1 | 8/2005 | Huang | |
| 2009/0277454 A1 | 11/2009 | Davis et al. | |

OTHER PUBLICATIONS

European Written Opinion for European Patent Appl. No. EP 09 25 1055.1, dated Aug. 4, 2009.

First office action for European Patent Appl. No. EP 09 25 1055.1, dated Jul. 8, 2010.

Second office action for European Patent Appl. No. EP 09 25 1055.1, dated Jul. 18, 2011.

* cited by examiner

GAS SUPPLY SYSTEM

This application is a continuation application of U.S. Non-provisional patent application Ser. No. 12/115,842 the present application claims benefit of the priority date of U.S. Non-provisional patent application Ser. No. 12/115,842 filed on May 6, 2008, the entire disclosure of which is herein incorporated by reference.

TECHNICAL FIELD & BACKGROUND

The present invention relates generally to delivery of therapeutic gases such as oxygen, nitrous oxide and the like to patients, and, more particularly, to a gas supply system capable of delivering a gas or a therapeutic gas from a gas supply to a nasal cannula connected to a patient's nose.

During surgeries and other medical treatments, patient often require a supply of therapeutic gases, for example, oxygen, nitrous oxide, and the like. A source of the therapeutic gases may include an air canister gas supply system, an air supply cylinder and the like. The therapeutic gases may be supplied to the patient from the source using a gas tube and a nasal cannula. More specifically, one end of the gas tube is connected to the source and the other end to the nasal cannula. Further, the nasal cannula is used to administer the therapeutic gases into the patient through their nose.

Moreover, when the gas tube is dragged along a dirty floor of the room due to the patient's movement, the gas tube may get soiled. Accordingly, the patient using such a soiled gas tube may catch infection. Further, the gas tube lying on the floor or dragged along the room may affect aesthetic appeal of the room and may provide an unorganized environment to the patient.

Accordingly, based on the foregoing, there is a need for a gas supply system that allows a patient to move freely and conveniently inside a room while being administered a therapeutic gas from the gas supply system. Moreover, the gas supply system should prevent a gas tube from lying on a floor of the room and being dragged along the floor. Further, there is a need for a gas supply system that keeps a gas tube clean, thereby reducing chances of causing infection to a patient. Furthermore, there is a need for a gas supply system that enables a user to preserve the aesthetics of the room, thereby providing an organized environment to the patient.

Accordingly, an object of the present invention is to provide a gas supply system that allows a patient to move freely and conveniently inside a room while being administered a therapeutic gas from the gas supply system.

Another object of the present invention is to provide a gas supply system that prevents a gas tube from lying on a floor of the room and being dragged along the floor.

Yet another object of the present invention is to provide a gas supply system that keeps a gas tube clean, thereby reducing chances of causing infection to a patient.

In light of the above objects, in one aspect of the present invention, a gas supply system is disclosed. The gas supply system is capable of delivering gas from a gas supply to a nasal cannula and capable of being removably mounted on a supporting member.

These together with other aspects of the present invention, along with a plurality of other features that characterize the present invention, are pointed out with particularity in the claims annexed hereto and form a part of this present invention. For a better understanding of the present invention, its operating advantages, and the specific objects attained by its uses, reference should be made to the accompanying drawings and descriptive matter in which there are illustrated exemplary embodiments of the present invention.

BRIEF DESCRIPTION OF THE DRAWINGS

The present invention will be described by way of exemplary embodiments, but not limitations, illustrated in the accompanying drawings in which like references denote similar elements.

Like reference numerals refer to like parts throughout the description of several views of the drawings.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
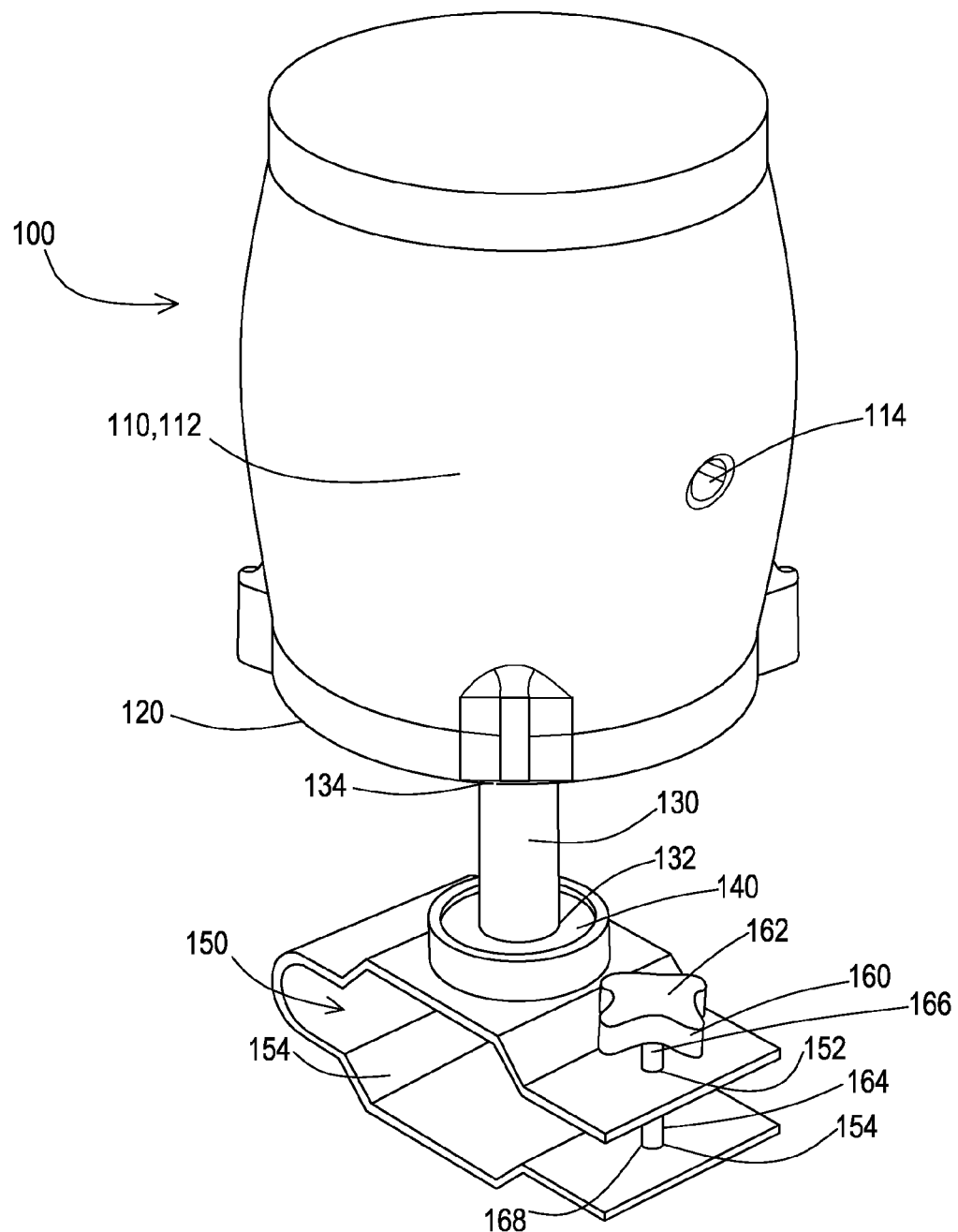
FIG. 1 illustrates a diagonal perspective view of a gas supply system, in accordance with an embodiment of the present invention.

FIG. 1 illustrates a gas supply system 100, in accordance with an embodiment of the present invention. The gas supply system 100 typically contains oxygen but can contain any suitable medical related gas.

The gas supply system 100 includes a housing 110, a main base 120, a rotating shaft 130, a rotational bearing 140, a base clamp 150 and an adjustable clamp screw 160. The housing 110 houses a plurality of gas supply canister components described and illustrated in FIG. 3 and its description. The housing 110 is generally cylindrical-shaped 112 but can be any suitable housing shape. The housing 110 also includes an aperture 114 to allow the gas tubing to pass therein and to be wound and unwound by the components described hereinafter and illustrated in FIG. 3. The main base 120 stabilizes the housing 110 in an upright perpendicular position. The rotating shaft 130 has a proximal end 132 and a distal end 134 where the main base 120 is disposed on the distal end 134 of the rotating shaft 130. The rotational bearing 140 is disposed on the proximal end 132 of the rotating shaft 130 and connects the rotating shaft 130 to the base clamp 150. The base clamp 150 has a pair of corresponding apertures 152, 154 and secures the gas supply system 100 to a tubular or other suitably shaped object (not shown) such as a bed post or bed frame. The base clamp 150 has one or more surfaces 170 for accommodating foam or other suitable padding between the base clamp 150 and the tubular or other suitably shaped object. The padding is disposed on the base clamp 150 to prevent damage to the base clamp 150 or the tubular or other suitably shaped object. The adjustable clamp screw 160 has a handle 162 and a threaded bolt 164 with a proximal end 166 and a distal end 168. The proximal end 166 of the threaded bolt 164 is attached to and perpendicularly extends from the handle 162. The adjustable clamp screw 160 is rotated and screwed through the pair of corresponding apertures 152, 154 of the base clamp 150 to tighten the base clamp 150 around the tubular or other suitably shaped object.

Figure 2A:
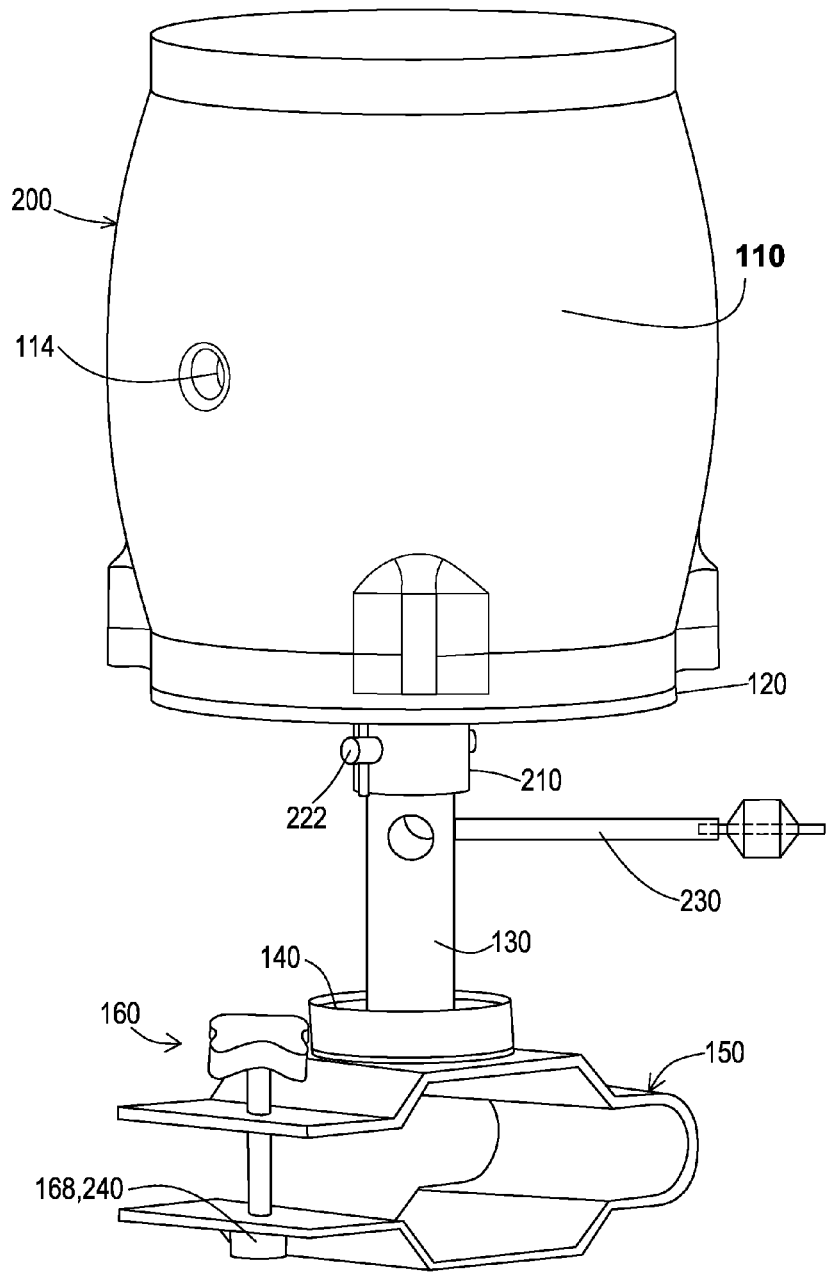
FIG. 2A illustrates a side perspective view of a gas supply system, in accordance with an embodiment of the present invention.

FIG. 2A illustrates a side perspective view of a gas supply system 200, in accordance with an embodiment of the present invention. The gas supply system 200 includes a plurality of similar components that are utilized and described and illustrated in FIG. 1 and its description and include a housing 110, a main base 120, a rotating shaft 130, a rotational bearing 140, a base clamp 150 and an adjustable clamp screw 160. The gas supply system 200 additionally includes a sleeve 210, a pin 222, and a receiving nut 240. The sleeve 210 is placed underneath the main base 120 on the rotating shaft 130 and includes a pair of corresponding apertures that also extend through the rotating shaft 130. The receiving nut 240 is disposed on the distal end 168 of the adjustable clamp screw 160 and assists in securing the adjustable clamp screw 160.

Figure 2B:
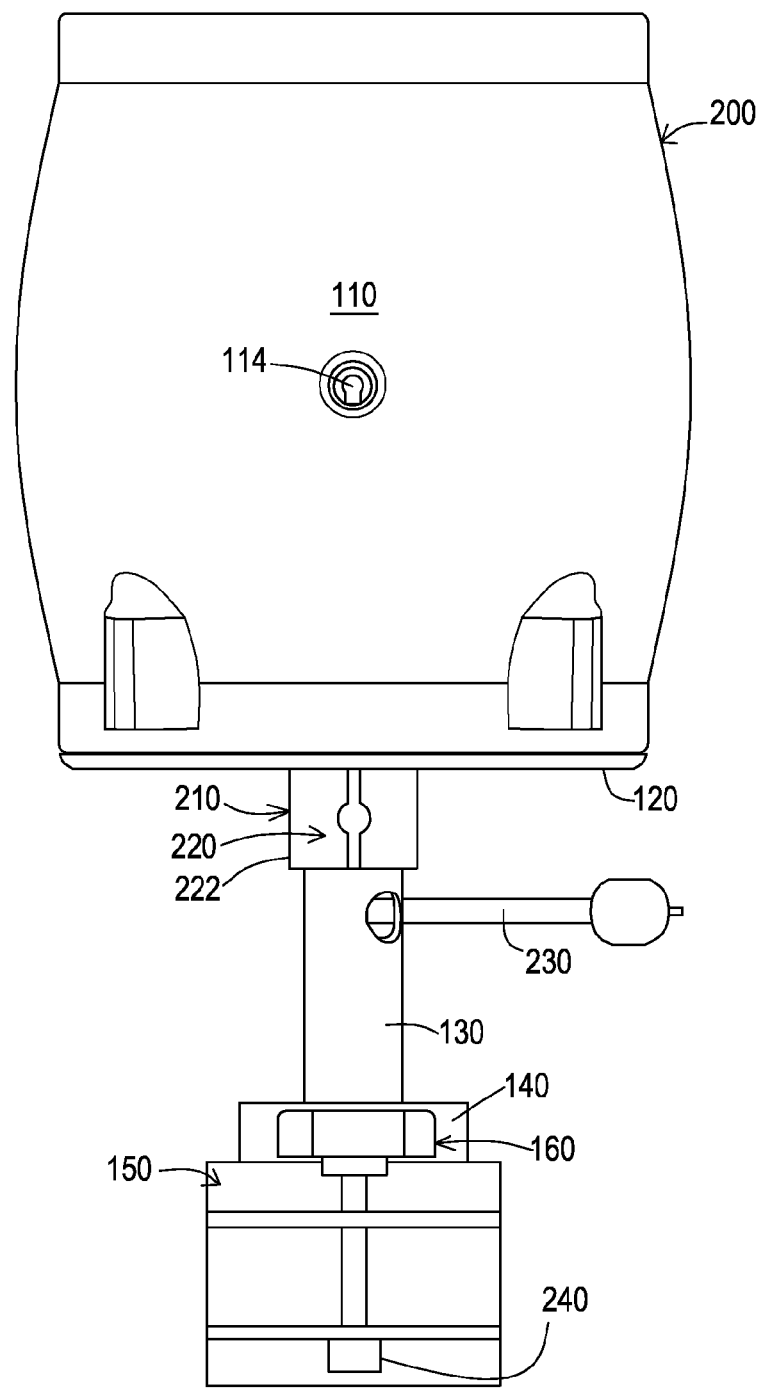
FIG. 2B illustrates a front perspective view of a gas supply system, in accordance with an embodiment of the present invention.

FIG. 2B illustrates a front perspective view of a gas supply system 200, in accordance with an embodiment of the present invention. The gas supply system 200 include a plurality of similar components that are utilized and described and illustrated in FIG. 1 and FIG. 2A and their description and include a housing 110, a main base 120, a rotating shaft 130, a rotational bearing 140, a base clamp 150 and an adjustable clamp screw 160. The gas supply system 200 additionally includes a sleeve 210, an elbow connector 220, an extended handle 230 and a receiving nut 240. The illustration in FIG. 2B also illustrates the housing 110 that also includes the aperture 114 previously described in FIG. 1 that will be discussed further and described and illustrated in FIG. 3 and it's description.

Figure 3:
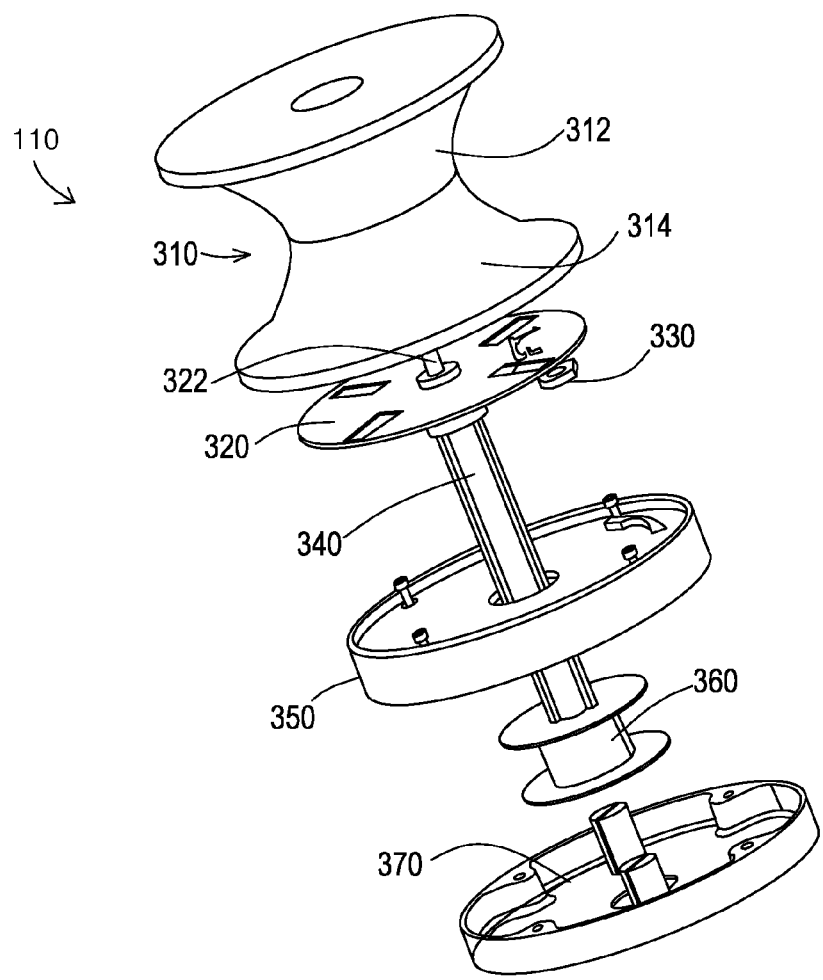
FIG. 3 illustrates an exploded view of a gas supply canister utilized by a gas supply system, in accordance with an embodiment of the present invention.

FIG. 3 illustrates an exploded view of a plurality of internal components of a housing 110 utilized by a gas supply system 100, 200, in accordance with an embodiment of the present invention. The internal components illustrated in FIG. 3 are disposed in the housing 110 illustrated in FIGS. 1 and 2, and include a spool 310, a one way bearing 320, an interval locking device 330, a universal shaft 340, an upper spring housing 350, a spring torque spool 360, and a lower spring housing 370 with a pair of spring grounding tabs 372. The spool 310, the one way bearing 320, the interval locking device 330, the universal shaft 340, the upper spring housing 350, the spring torque spool 360 and the lower spring housing 370 are all contained in the housing 110. The spool 310 has a top portion 312 and a bottom portion 314 that receives and winds gas tubing, which is typically oxygen gas tubing, within the housing 110. The spool 310 receives the gas tubing from the aperture 114 described and illustrated in FIG. 1. The one way bearing 320 is set under the spool 310 on a small shaft 322 underneath the spool 310. The interval locking device 330 locks the typically oxygen gas tubing in place at a plurality of locations or intervals along the rotation of the spool. The universal shaft 340 encapsulates the small shaft 322 underneath the spool 310. The upper spring housing 350 is placed on the universal shaft 340 underneath the interval locking device 330 and houses a spring. The spring torque spool 360 secures one of the spring's free ends, rotates with the universal shaft 340, and is disposed at the bottom of the universal shaft 340. The lower spring housing 370 includes a pair of spring grounding tabs 372.

The present invention provides a gas supply system. The gas supply system is adapted to be used for delivery of a gas from a gas supply, for example, an air supply cylinder, to a nasal cannula. The gas supply system enables the patient to move conveniently and freely from one place to another inside a room while being administered a gas from the disclosed gas supply system. Moreover, the gas supply system prevents the tube from lying on a floor of the room and being dragged thereof along the floor.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A gas supply system, comprising:
   a housing that includes an aperture, a spool, a one way bearing circumscribing a vertically-oriented small shaft, an interval locking device, a vertically-oriented universal shaft, a spring housing, and a spring torque spool configured to secure a free end of a spring;
   a main base that stabilizes said housing in an upright perpendicular position;
   a vertically-oriented rotating shaft that has a proximal end and a distal end where said main base is disposed on said distal end of said vertically-oriented rotating shaft;
   a base clamp having a top surface and a pair of corresponding apertures, said base clamp configured to secure said gas supply system to a tubular shaped object;
   a rotational bearing that is disposed on said top surface of said base clamp and at said proximal end of said vertically-oriented rotating shaft, said rotational bearing connecting the vertically-oriented rotating shaft to said base clamp; and
   an adjustable clamp screw that has a handle and a threaded bolt with a proximal end and a distal end wherein said proximal end of said threaded bolt is attached to and perpendicularly extends from said handle of said adjustable clamp screw.

2. The system according to claim 1, wherein said housing is generally cylindrical-shape.

3. The system according to claim 1, wherein said base clamp is configured to support padding disposed thereon, said padding configured to prevent damage to said base clamp or said tubular shaped object.

4. The system according to claim 1, wherein said adjustable clamp screw is rotated and screwed through said pair of corresponding apertures of said base clamp to tighten said base clamp around said tubular or other suitably shaped object.

5. The system according to claim 1, wherein said spool has a top inverted frusto-conical portion and a bottom frusto-conical portion, said top inverted frusto-conical portion being disposed at a higher elevation than said bottom frusto-conical portion relative to a horizontal reference plane beneath said gas supply system, said spool being configured to receive and wind oxygen gas tubing within said housing from said aperture.

6. The system according to claim 5, wherein said interval locking device is disposed between an upper portion of said spring housing and said one way bearing, said interval locking device configured to lock said oxygen gas tubing at a plurality of locations or intervals along the rotation of said spool.

7. The system according to claim 5, wherein said spring housing is placed on said vertically-oriented universal shaft underneath said interval locking device such that said spring housing is disposed at a lower elevation than said interval locking device relative to a horizontal reference plane beneath said gas supply system, said spring housing configured to house said spring.

8. The system according to claim 1, wherein said vertically-oriented universal shaft encapsulates said vertically-oriented small shaft underneath said spool, said vertically-oriented universal shaft having one or more elongated protruding portions extending radially outward from a circumferential surface thereof.

9. The system according to claim 1, wherein said one way bearing is set under said spool on said vertically-oriented small shaft such that said one way bearing is disposed at a lower elevation than said spool relative to a horizontal reference plane beneath said gas supply system.

10. The system according to claim 1, wherein said spring torque spool rotates with said universal shaft and is disposed at a bottom of said vertically-oriented universal shaft.

11. The system according to claim 1, wherein said gas supply system includes a sleeve disposed underneath said main base such that said sleeve is disposed at a lower elevation than said main base relative to a horizontal reference plane beneath said gas supply system, said sleeve being attached to said distal end of said vertically-oriented rotating shaft by a pin.

12. The system according to claim 1, wherein said gas supply system includes a receiving nut.

13. A gas supply system, comprising:
a housing that includes an aperture, a spool, a one way bearing circumscribing a vertically-oriented small shaft, an interval locking device, a vertically-oriented universal shaft, a spring housing, and a spring torque spool configured to secure a free end of a spring, said spring torque spool configured to rotate with said vertically-oriented universal shaft;
a main base that stabilizes said housing in an upright perpendicular position;
a sleeve disposed underneath said main base such that said sleeve is disposed at a lower elevation than said main base relative to a horizontal reference plane beneath said gas supply system;
a vertically-oriented rotating shaft having a proximal end and a distal end, said main base being disposed proximate to said distal end of said vertically-oriented rotating shaft, and said distal end of said vertically-oriented shaft being attached to said sleeve by a pin;
a base clamp having a top surface and a pair of corresponding apertures, said base clamp configured to secure said gas supply system to a tubular shaped object;
a rotational bearing that is disposed on said top surface of said base clamp and at said proximal end of said vertically-oriented rotating shaft, said rotational bearing connecting the vertically-oriented rotating shaft to said base clamp; and
an adjustable clamp screw that has a handle and a threaded bolt with a proximal end and a distal end wherein said proximal end of said threaded bolt is attached to and perpendicularly extends from said handle of said adjustable clamp screw.

14. The system according to claim 13, wherein said spring housing comprises a top portion and a bottom portion, said top portion of said spring housing being disposed at a higher elevation than said bottom portion of said spring housing relative to a horizontal reference plane beneath said gas supply system.

15. The system according to claim 13, wherein said handle of said adjustable clamp screw comprises a plurality of convex indentations disposed about a periphery thereof.

16. The system according to claim 13, wherein said vertically-oriented universal shaft encapsulates said vertically-oriented small shaft underneath said spool, said vertically-oriented universal shaft having one or more elongated protruding portions extending radially outward from a circumferential surface thereof.

17. A gas supply system, comprising:
a housing that includes an aperture, a spool, a one way bearing circumscribing a vertically-oriented small shaft, an interval locking device, a vertically-oriented universal shaft, a spring housing, and a spring torque spool configured to secure a free end of a spring, said spring torque spool configured to rotate with said vertically-oriented universal shaft;
a main base that stabilizes said housing in an upright perpendicular position;
a sleeve disposed underneath said main base such that said sleeve is disposed at a lower elevation than said main base relative to a horizontal reference plane beneath said gas supply system;
a vertically-oriented rotating shaft having a proximal end and a distal end, said main base being disposed proximate to said distal end of said vertically-oriented rotating shaft, and said distal end of said vertically-oriented shaft being attached to said sleeve by a pin;
a base clamp having a top surface and a pair of corresponding apertures, said base clamp configured to secure said gas supply system to a tubular shaped object;
a rotational bearing that is disposed on said top surface of said base clamp and at said proximal end of said vertically-oriented rotating shaft, said rotational bearing connecting the vertically-oriented rotating shaft to said base clamp; and
an adjustable clamp screw that has a handle and a threaded bolt with a proximal end and a distal end wherein said proximal end of said threaded bolt is attached to and perpendicularly extends from said handle of said adjustable clamp screw, said handle of said adjustable clamp screw including a plurality of convex indentations disposed about a periphery thereof.

18. The system according to claim 17, wherein said spool has a top inverted frusto-conical portion and a bottom frusto-conical portion, said top inverted frusto-conical portion being disposed at a higher elevation than said bottom frusto-conical portion relative to a horizontal reference plane beneath said gas supply system, said spool being configured to receive and wind oxygen gas tubing within said housing from said aperture.

19. The system according to claim 17, wherein said spring housing comprises a top portion and a bottom portion, said top portion of said spring housing being disposed at a higher elevation than said bottom portion of said spring housing relative to a horizontal reference plane beneath said gas supply system.

20. The system according to claim 17, wherein said vertically-oriented universal shaft encapsulates said vertically-oriented small shaft underneath said spool, said vertically-oriented universal shaft having one or more elongated protruding portions extending radially outward from a circumferential surface thereof.

* * * * *